(12) United States Patent
Molock et al.

(10) Patent No.: US 9,297,928 B2
(45) Date of Patent: Mar. 29, 2016

(54) OPHTHALMIC COMPOSITIONS COMPRISING POLYETHER SUBSTITUTED POLYMERS

(75) Inventors: Frank Molock, Orange Park, FL (US); Kathrine Osborn Lorenz, Columbus, OH (US); Shivkumar Mahadevan, Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 2627 days.

(21) Appl. No.: 10/994,717

(22) Filed: Nov. 22, 2004

(65) Prior Publication Data

US 2006/0110427 A1    May 25, 2006

(51) Int. Cl.
*A61K 31/785* (2006.01)
*A61K 31/74* (2006.01)
*A61F 2/00* (2006.01)
*G02B 1/04* (2006.01)

(52) U.S. Cl.
CPC ...................................... *G02B 1/041* (2013.01)

(58) Field of Classification Search
None
See application file for complete search history.

(56) References Cited

U.S. PATENT DOCUMENTS

| | | | |
|---|---|---|---|
| 4,287,175 A | 9/1981 | Katz | |
| 4,638,040 A * | 1/1987 | Hammar | 526/245 |
| 4,775,531 A | 10/1988 | Gilbard | |
| 5,106,615 A | 4/1992 | Dikstein | |
| 5,290,548 A | 3/1994 | Goldberg | |
| 5,944,853 A | 8/1999 | Molock et al. | |
| 6,087,462 A | 7/2000 | Bowers | |
| 6,287,707 B1 | 9/2001 | Luthra et al. | |
| 6,384,111 B1 | 5/2002 | Kistenmacher et al. | |
| 6,406,687 B1 | 6/2002 | Luthra et al. | |
| 6,440,366 B1 | 8/2002 | Salpekar | |
| 6,444,780 B1 | 9/2002 | Kinoshita et al. | |
| 6,465,056 B1 | 10/2002 | Chabrecek | |
| 6,589,665 B2 | 7/2003 | Chabrecek | |
| 6,730,366 B2 | 5/2004 | Lohmann | |
| 6,740,317 B1 | 5/2004 | Cho et al. | |
| 6,740,703 B2 | 5/2004 | Sarkar et al. | |
| 6,749,836 B1 | 6/2004 | Chen et al. | |
| 2002/0197299 A1 * | 12/2002 | Vanderlaan et al. | 424/429 |
| 2003/0021762 A1 | 1/2003 | Luthra et al. | |
| 2003/0055135 A1 | 3/2003 | Alford | |
| 2003/0162862 A1 | 8/2003 | McCabe | |
| 2004/0116564 A1 | 6/2004 | Devlin et al. | |
| 2004/0137079 A1 | 7/2004 | Cook et al. | |

FOREIGN PATENT DOCUMENTS

| | | |
|---|---|---|
| EP | 537972 B1 | 7/1996 |
| JP | 2000010055 A | 1/2000 |
| JP | 2000169387 A | 6/2000 |
| JP | 2002256030 A | 9/2002 |
| WO | WO 8404681 A1 | 12/1984 |
| WO | WO 9620919 A1 | 7/1996 |
| WO | WO 99/30716 A1 | 6/1999 |
| WO | WO 03077792 A2 | 9/2003 |
| WO | WO 2004/055148 | 7/2004 |
| WO | WO 2004062660 A1 | 7/2004 |

OTHER PUBLICATIONS

PCT International Search Report, dated Apr. 6, 2006, for PCT Int'l. Appln. No. PCT/US2005/040836.
J.V. Crivello & K. Dietliker, vol. III, Photoinitiators for Free Radical Cationic & Anionic Photopolymerization, $2^{nd}$ Edition by edited by G. Bradley; John Wiley and Sons; New York; 1998.
Allen, M., Wright, P., Reid, L, The Human Lacrimal Gland, *Archives of Ophthalmology*, Nov. 1972, 493-497, 88.
Belley, D., Chadee K, Prostagalndin $E_2$ Stimulates Rat and Human Colonic Mucin Exocytosis Via the $EP_4$ Receptor, *Gastroenterology*, Dec. 1999, 1352-1362, 117(6).
Boshell, M., Lalani, E.N., Pemberton, L., Burchell, J., Gendler, S., Taylor, P.J., The Product of the Human MUC1 Gene when Secreted by Mouse Cells Transfected with the Full-Length cDNA Lacks the Cytoplasmic Tail, *Biochemical & Biophysical Research Communication*, May 29, 1992, 1-8, 185(1).
Brockhausen, I., Clinical Aspects of Glycoprotein Biosynthesis, *Critical Reviews in Clinical Laboratory Sciences*, 1993, 65-151, 30(2).
Bron, A.J., Non-Sjogren Dry Eye: Pathogenesis Diagnosis & Animal Models, *Advance in Experimental & Biology*, "Proceeding of an International Conference in the Lacrimal Gland, Tear Film, & Dry Eye Syndromes: Basic Science & Clinical Relevance, held Nov. 14-17, 1992, in Southhampton, Bermuda", 1994, 471-488, 350, Plenum Press, New York & London.
Bron, A.J., Duke-Elder Lecture: Prospects for Dry Eye, *Transactions of the Ophthalmological Societies of the UK*, 1985, 801-826, 104 Part VIII.
C.S. Patrickios, W.R. Hertler, N.L. Abbot, and T.A. Hatton, Diblock, ABC Triblock, & Random Methacrylic Polyampholytes: Synthesis by Group Transfer Polymerization and Solution Behavior, *Macromolecules*, Jan. 3, 1994, 930-937, 27(1).
Carlstedt, I., Sheehan, J.K., Corfield, A.P., Gallagher, J.T., Mucous Glycoproteins: A Gel of a Problem, *Essays in Biochemistry*, 1985, 40-76, 20.
Corfield, A.P., Carrington, S.D., Hicks, S.J., Berry, M., Ellingham, R., Ocular Mucins: Purification, Metabolism and Functions, *Progress in Retinal and Eye Research*, 1997, 627-656 16(4).
D.A. Benedetto, D.O. Shah, and H.E. Kaufmann, The Dynamic Film of Cushioning Agents on Contact Lens Materials, Annuals of Ophthalmology, Apr. 1978, 437-442, 10 (1).
D.Y. Sogah and W.R. Hertler, O.W. Webster, G.M. Cohen, Group Transfer Polymerization. Polymerization of Acrylic Monomers, *Macromolecules*, Jul. 1987, 1473-1488, 20(7).

(Continued)

*Primary Examiner* — Walter Webb
(74) *Attorney, Agent, or Firm* — Karen A. Harding

(57) ABSTRACT

The present invention relates to ophthalmic solutions and devices comprising at least one water soluble polymer having a molecular weight of at least about 500,000 Daltons and linear or branched polyether pendant groups having a molecular weight of at least about 300.

14 Claims, No Drawings

(56) References Cited

OTHER PUBLICATIONS

Dilly, P.N., On the Nature and the Role of the Subsurface Vesicles in the Outer Epithelial Cells of the Conjunctiva, *British Journal of Ophthalmology Editorial Committee*, 1985, 477-481, 69.

Dilly, P.N., Structure and Function of the Tear Film, *Lacrimal Gland, Tear Film, and Dry Eye Syndromes*, 1994, 239-247, Plenum Press, New York, USA.

Ellingham, R.B., Myerscough, N., Gout, I.I., Berry, M; Corfield, A.P., Soluble Mucins in Human Aqueous Tears, *Biochemical Society Transactions*, 659th Meeting Queen Mary & Westfield College, University of London, Feb. 1997, 12S, 25(1).

Fischer, B. & Voynow J., Neutrophil Elastase Induces MUC5AC Messenger RNA Expression by an Oxidant-Dependent Mechanism, *Chest*, May 2000, 317S-320S, 117(5) Supplement 1.

F.J. Holly & M.A. Lemp, Wettability & Wetting Corneal Epithelium, *Experimental Eye Research*, 1971, 239-250, 11.

F.J. Holly, Physical Chemistry of the Normal and Disordered Tear Film, *Transactions of the Ophthalmology Societies of the UK*, 1985, 374-380, 104(Part4).

F.J. Holly, Formation & Rupture of the Tear Film, *Experimental Eye Research*, May 1973, 515-525, 15(4), Academic Press, London and New York.

F.J. Holly, Formation & Stability of the Tear Film, *The Preocular Tear Film & Dry Eye Syndromes, International Ophthalmology Clinics*, Spring 1973, 73-96, 13(1).

F.J. Holly, M.J. Refojo, Water Wettability of Proteins Absorbed at the Hydrogel Water Interface, *Hydrogels for Medical & Related Application, ACS Symposium Series*, 1976, Chapter 20, 267-282, 31, American Chemical Society, Washington DC, USA.

Fontenot, J.D., Tjandra, N., BU, D., HO, C., Montelar, R.C., & Finn O.J., Biophysical Characterization of One-, Two-, and Three-Tandem Repeats of Human Mucin (muc-1) Protein Core, Cancer Research, Nov. 15, 1993, 5386-5394, 53(22).

Fujihara, T., Murakami M., Nakamura, K, Potential Therapeutic Value of the P2Y2 Receptor Agonist, INS365, in Dry Eye Treatment, *3rd International Symposium on Ocular Pharmacology and Pharmaceutics* (ISOPP), Feb. 10-13, 2000, Lisbon, Portugal, http://www.kenes.com/isopp3/prs11.htm.

Peter Y.S. Fung & B. Michael Longnecher, Specific Immunosuppressive Activity of Epiglycanin, a Mucin-like Glycoprotein Secreted by a Murine Mammary Adenocarcinoma (TA3-HA)1, *Cancer Research*, Feb. 15, 1991, 1170-1176, 51(4).

G.K Yamamoto, M. R. Allansmith, Complete in Tears from Normal Humans, American Journal of Ophthalmology, Jul.-Dec. 1979, 758-763, 88(4).

Gendler, S.J., Burchell, J.M., Duhig, T., Lamport, D., White, R., Parker M., Cloning of Partial cDNA Encoding Differentiation & Tumor-Associated Mucin Glycoproteins Expressed by Human Mammary Epithelium, Proceedings of the National Academy of Sciences the USA, Sep. 1987, 6060-64, 84(17).

Gendler, S.J., Spicer, A.P., Epithelial Mucin Genes, *Annual Review of Physiology*, 1995, 607-634, 57.

Gipson, I.K., Inatomi, T., Cellular Origin of Mucins of the Ocular Surface Tear Film, *Lacrimal Gland, Tear Film, and Dry Eye Syndromes 2: Basic Science & Clinical Relevance*, 1998, Chapter 32, 221-227, Plenum Press, New York, USA.

Gipson, I.K., Inatomi, T., Mucin Genes Expresses by the Ocular Surface Epithelium, *Progress Retinal Eye Research*, 1997, 81-98, 16(1).

Gipson, I.K., Spurr-Michaud, S.J., Tisdal, A.S., Kublin, C., Cintron, C., Keutmann, H., Stratified Squamous Epithelia Produce Mucin-Like Glycoproteins, *Tissue & Cell*, Aug. 1995, 397-404, 27(4).

Gipson, I.K., Yankauckas, M., Spurr-Michaud, S.J., Tisdale, A.S., Rinehart, W., Characteristics of a Glycoprotein in the Ocular Surface Glycocalyx, Investigative Ophthalmology & Visual Science, Jan. 1992, 218-227, 33(1).

Greiner, J.V., Weidman, T.A, Korb, D.R., Allansmith, M.R., Histochemical Analysis of Secretory Vesicles in Nongoblet Conjunctival Epithelial Cells, Acta Ophthalmologica, 1985, 89-92, 63.

Griffin, W.C., Calculation of HLB Values of Non-Ionic Surfactants, Journal of the Society of Cosmetic Chemists, Mar. 1954, 249-256, 5(1).

Gum, J.R. Jr., Mucin Genes & the Proteins They Encode: Structure, Diversity & Regulation, *American Journal of Respiratory Cell & Molecular Biology*, 1992, 557-564, 7.

Gum, J.R. Jr., Hicks, J.W., Toribara, N.W., Siddiki, B., Kim, Y.S., Molecular Cloning of Human Intestinal Mucin (MUC2) cDNA, *Journal of Biological Chemistry*, Jan. 28, 1994, 2440-2446, 269(4).

Gunduz, K., & Ozden O., Topical Cyclosporin Treatment of Keratoconjunctivitis Sicca in Secondary Sjogren's Syndrome, *ACTA Ophthalmologica*, Aug. 1994, 438-442, 72(4).

H.S. Yu, W.J. Choi, K.T. Lim, and S.K Choi, Group Transfer Polymerization by Bifunctional Initiators: A Simple Method for ABA Triblock Copolymers, *Macromolecules*, Sep. 1988, 2893-2894, 21(9).

Holly, F.J., Lemp, M.A., Tear Physiology & Dry Eye, *Survey of Ophthalmology*, 1977-1978 (Sep.-Oct. 1977), 69-87, 22(2).

Hong, D.-H., Petrovics, G., Anderson, W.B., Forstner J., & Forstner G., Induction of Mucin Gene Expression in Human Colonic Cell Lines by PMA is Dependent to PKC-ε, *American Journal of Physiolology*, Nov. 1999, G1041-G1047, 227(5).

Ichikawa, T., Endoh, H., Hotta, K., Ishihara, K., The Mucin Biosynthesis Stimulated by Epidermal Growth Factor Occurs in Surface Mucus Cells, but not in Gland Mucus Cells, of Rat Stomach, *Life Sciences*, 2000, 1095-1101, 67.

Ichikawa, T., Ishihara, K., Hayashida, H., Hiruma, H., Saigenji, K., Hotta, K., Effects of Ecabet Sodium, a Novel Gastroprotective Agent, on Mucin Metabolism in Rat Gastric Mucosa, *Digestive Diseases and Sciences*, Mar. 2000, 606-613, 45(3).

Inatomi, T., New Unsights into Tear Mucous Layer, *Atarashii Ganka; Special features: Tears-Aspects and Concepts*, 1997, 1637-1645, 14(11).

Inatomi, T., Spurr-Michaud, S., Tisdale, A.S., Zhan, Q., Feldman, S.T., Gipson, I.K., Expression of Secretory Mucin Genes by Human Conjunctival Epithelia, *Investigative Ophthalmology, & Visual Science*, Jul. 1996, 1684-1692, 37(8).

J. Purcell, S.P. Armes, and N.C. Billingham, ABA Triblock Copolymers via Group Transfer Polymerisation, *Polymer Preprints*, Apr. 1997, 502-3, 38(1).

J.E. McDonald, Surface Phenomena of the Tear Film, *American Journal of Ophthalmology*, Jan.-Jun. 1969 (Jan.), 56-64, 67.

Jensen, O.A., Falbe-Hansen, I., Jacobsen, T., Michelson, A., Mucosubstances of the Acini of Human Lacrimal Gland (Orbital Part), Acta. Ophthalmotogica, 1969, 605-619, 47(III).

K. Steinbrecht, and F. Bandermann, Bifunctional Initiators for Group Transfer Polymerization, Die Makromolekulare Chemie, Sep. 1989, 2183-2191, 190 (9-12).

K.C. Swan, Use of Mehtyl Cellulose in Ophthalmology, Archives of Ophthalmology, 1945, 378-380, 33.

Kessler, T.L., Mercer, H.J., Zieske, J.D., Mccarthy, D.M., Dartt, D.A., Stimulation of Goblet Cell Mucous Secretion by Activation of Nerves in Rat Conjunctiva, *Current Eye Research*, 1995, 985-992, 14.

Kinoshita, S., Kiorpes, T.C., Friend, J., Thoft, R.A., Goblet Cell Density in Ocular Surface Disease: A Better Indicator than Tear Mucin, Archives of Ophthalmology, Aug. 1983, 1284-1287, 101(8).

Kreuger, J., Sokoloff, N., Botelho, S.Y., Sialic Acid in Rabbit Lacrimal Gland Fluid, *Investigative Ophthalmology*, 1976, 479-481, 15(1).

Kubo, Y., Arimura, A., Nakayasu, K., Kanai, A., Effect of Vitamin A Palmitate on the Synthesis of Mucins in Cultured Conjunctiva, *Journal of Japanese Ophthalmological Society Nippon Ganka Gakkai Zasshi*, Aug. 1999, 580-583, 103(8).

Lemp, M.A., The Mucin-Deficient Dry Eye, *The Preocular Tear Film & Dry Eye Syndromes: International Ophthalmology Clinics*, Spring 1973, 185-189, 13(1).

Lightenberg, M.JL., Buijs, F., Vos, H.L., Hilkens, J., Suppression of Cellular Aggregation by High Levels of Episialin, *Cancer Research*, Apr. 15, 1992, 2318-2324, 52(8).

(56) References Cited

OTHER PUBLICATIONS

Louahed, J., Toda, M., Jen, J., Hamid, Q., Renauld, J-C., Levitt, R.C., Nicolaides N.C., Interleukin-9 Upregulates Mucus Expression in the Airways, *American Journal of Respiratory Cell and Molecular Biology*, 2000, 649-656, 22.

Lowther, G.E., Handling Hydrogel Lens Patients with Contact Lens-Tear Film Problems, *Dryness, Tears, and Contact Lens Wear: Clinical Practice in Contact Lenses*, 1997, 54-56, Butterworth-Heinemann, Boston, MA, USA.

M.A. Lemp and E.S. Szymanski, Polymer Absorption at the Ocular Surface, *Archives of Ophthalmology*, Feb. 1975, 134-136, 93, American Medical Association Publication.

M.A. Muller and M. Stickler, On Tacticity of Poly(methyl methacrylate) Prepared by Group Transfer Polymerization, *Die Makromolekulare Chemie Rapid Communications*, 1986, 575-583, 7.

N. Nicolaides, Meibomian Gland Studies: Comparison of Steer and Human Lipids, *Investigative Ophthalmic & Visual Science*, Apr. 1981, 522-536, 20(4).

Nakamura, M., Endo, K-I., Nakata, K., Mucin-like Glycoprotein Secretion is Mediated by Cyclic-AMP & Protein Kinase C Signal Transduction Pathways in Rat Corneal Epithelium, *Experimental Eye Research*, 1998, 513-519, 66.

Nakamura, M., Endo, K-I., Nakata, K., Hamano, T., Gefamate Stimulates Secretion of Mucin-Like Glycoproteins by Corneal Epithelium in Vitro & Protects Corneal Epithelium from Desiccation in Vivo, *Experimental Eye Research*, 1997, 569-574, 65.

Nakamura, M., Endo, K-I., Nakata, K., Hamano, T., Gefarnate Increases PAS Positive Cell Density in Rabbit Conjunctiva, *British Journal of Ophthalmology*, Nov. 1998, 1320-1323, 82(11).

Nelson, J.D., Wright, J.C., Conjunctival Goblet Cell Densities in Ocular Surface Disease, *Archives of Ophthalmology*, Jul. 1984, 1049-1051, 102(7).

O. Tsutsumi, A Tsutsumi, T Oka, Epidermal Growth Factor-Like, Corneal Wound Healing Substance in Mouse Tears, *Journal of Clinical Investigation*, Apr. 1988, 1067-1071, 81(4).

O.W. Webster, The Use of Group Transfer Polymerization for the Control of Polymethacrylate Molecular Structure, *Die Makromolekulare Chemie Macromolecular Symposia*, 1990, 133-143, 33.

O.W. Webster, W.R. Hertler, D.Y. Sogah, W.B. Farnham and T.V. Rajanbabu, Group-Transfer Polymerization. 1. A New Concept for Addition Polymerization with Organosilicon Initiators, *Journal of the American Chemical Society*, Aug. 24, 1983, 5706-5708, 105(17).

Oechsner, M., Keipert S., Polyacrylic Acid/Polyvinylpyrrolidone Bipolymeric Systems. European Journal of Pharmaceutics and Biopharmaceutics, 1999, 113-118, 47(2).

P. Mai and A.H. Muller, Kinetics of Group Transfer Polymerization of Methyl Methacrylate in Tetrahydrofuran, *Die Makromolekulare Chemie Rapid Communications*, 1987, 247-253, 8.

Patel, S., The Management of Dry-Eye Problems, Optician, Feb. 2, 2001, 26-32, 221(5786).

Phillips, T., McHugh, J., Moore C., Cyclosporine Has a Direct Effect on the Differentiation of a Mucin-Secreting Cell Line, *Journal of Cellular Physiology*, Sep. 2000, 400-408, 184(3).

Plantner, J.J., High Molecular Weight Mucin-Like Glycoproteins of the Bovine Interphotoreceptor Matrix, Experimental Eye Research, 1992, 113-125, 54.

Prydall, J.J., Campbell F.W., Study of Precorneal Tear Film Thickness & Structure by Interferometry & Confocal Microscopy, Investigative Ophthalmology Visual Science, May 1992, 1996-2005, 33(6).

R. Freitag, T. Baltes, and M. Eggert, A Comparison of Thermoreactive Water-Soluble Poly-N,N-diethylacrylamide Prepared by Anionic and by Group Transfer Polymerization, Journal of Polymer Science, Part A: Polymer Chemistry, 1994, 3019-3030, 32(13).

R.A. Ralph, Conjunctival Goblet Cell Density in Normal Subjects and in Dry Eye Syndromes, *Investigative Ophthalmology*, Apr. 1975, 299-302, 14(4).

Rice, G.E., Bevilacqua, M.P., An Inducible Endothelial Cell Surface Glycoprotein Mediated Melanoma Adhesion, *Science*, Dec. 8, 1989, 1303-1306, 246.

S. Mishima, Some Physiological Aspects of Precorneal Tear Film, *Archives of Ophthalmology*, Feb. 1965, 233-241, 73.

Shanker, R.M., Ahmed, I., Bourassa, P.A., Carola, KV., An in Vitro Technique for Measuring Contact Angles on the Corneal Surface & its Application to Evaluate Corneal Wetting Properties of Water Soluble Polymers, *International Journal of Pharmaceutics*, 1995, 149-163, 119(2).

Shimuzu, Y., Shigemitsu, T., Majima, Y., Basic Experiment with Mucin Ophthalmic Solution: Effect on Healing of Rabbit Corneal Epithelial Damage, *Atarishi Ganka (Journal of the Eye)*, 1995, 1601-1605, 12(10).

Shoji, J., Sakimoto, T., Kitano, S., Ishii, Y., Trapping Role in Mucin, *Nippon Ganka Gakkai Zasshi (ACTA Soc. Ophthalmol Jpn)*, 1988, 2038-2047, 92(12).

Srinivasan, B.D., Worgul, B. V., Iwamoto, T., Merriam, G.R. Jr., The Conjunctival Epithelium, *Ophthalmic Research*, 1977, 65-79, 9(2).

Strouss, G.J., Dekker, J., Mucin-Type Glycoproteins, *Critical Reviews in Biochemistry and Molecular Biology*, 1992, 57-92, 27(1,2).

Takeyama, K., Dabbagh, K., Lee, H-M., Agusti, C., Lausier, J., Ueki, I., Grattan, K., Nadel, J., Epidermal Growth Factor System Regulates Mucin Production in Airways, *Proceeding of the National Academy of Sciences of the United States of American*, Mar. 16, 1999, 2571-3330, 96(6).

Tiffany, J.M., Pandit, J.C., Bron, A., Soluble Mucin & the Physical Properties of Tears, *Lacrimal Gland, Tear Film, and Dry Eye Syndromes 2*, 1998, 229-234, Plenum Press, New York, USA.

Tokushige, H., Naka, H., Ohtori, A., Effect of Ecabet Sodium on Secretion of Mucin-Like Glycoproteins in Ocular Surfaces, $3^{rd}$ *International Symposium on Ocular Pharmacology and Pharmaceutics (ISOPP)*, Feb. 10-13, 2000, Lisbon, Portugal, http://www.kenes.com/isopp3/prs11.htm.

Trueblood, J.H., Rossomondo, R.M., Carlton, W.H., Wilson, L.S., Corneal Contact Times of Ophthalmic Vehicles, *Archives of Ophthalmology*, Feb. 1975, 127-130, 93.

Tsuyama, N. et al, On the Mechanism of Deposition and Quantification of Mucin Deposited on Hydrophilic Soft Contact Lenses, *Nippon Kontakuto Renzu Kaishi (Journal of Japan Contact Lens Society*, 1996, 153-158, 38(3).

Van Klinken, B.J.W., Jan-Willem B., Dekker, J., Buller, H.A., Einerhand, A.W.C., Mucin Gene Structure & Expression: Protection vs. Adhesion, *American Journal of Physiology*, 1995, G613-G627, 269.

W. J. Choi, K.W. Lim, S.K. Kwon, and S.K. Choi, Synthesis & Characterization of ABA Triblock Copolymers of 2-Hydroxyethyl Methacrylate & n-Butyl Methacrylate by Group Transfer Polymerization, *Polymer Bulletin*, 1993, 401-406, 30.

W. Schubert, H-D Sitz, and F. Bandermann, Group Transfer Polymerization of Methyl Methacrylate & Methyl Acrylate in Tetrahydrofuran with Tris(Piperridino)Sulfonium Bifluoride as Catalyst, *Die Makromolekulare Chemie*, 1989, 2193-2201, 190(9-12).

Watanabe, H., Fabricant, M., Tisdale, A.S., Spurr-Michaud, S.J., Lindberg, K., Gipson, I.K., Human Corneal & Conjuctival Epithelia Produce a Mucin-like Glycoprotein for the Apical Surface, *Investigative Ophthalmology & Vision Sciences*, 1995, 337-344, 36(2).

Watanabe, H., Mucin Layer Disorder & their Treatment—Mucin Deficiency & its Treatment—Special Series: On Tear Film, Atarashii Ganka, 1997, 1647-1653, 14(11).

Wei, J.G., Sun, T.T., Lavker, R.M., Keratinocytes & Goblet Cells of the Rabbit Conjunctival Epthelium Share a Common Progenitor Cell, *Investigative Ophthalmology & Visual Science-Abstract Book*, Mar. 15, 1995, S422(1938-12:00), 36(4).

Wright, P., Mackie, I.A., Mucus in the Healthy & Diseased Eye, *Transactions of the Ophthalmolgical Societies of the U.K.—Proceeding of the 97th Annul Congress*, Apr. 13 to 15, 1977, 1-7, 97(1).

Y. Ohashi, M. Motokura, Y. Kinoshita, T. Mano, H. Watanabe, S. Kinoshita, R. Manabe, K. Oshiden, C. Yanaihara, Presence of Epidermal Growth Factor in Human Tears, *Investigative Ophthalmology Visual Science*, Aug. 1989, 1879-1882, 30(8).

(56) References Cited

OTHER PUBLICATIONS

Yoon, J-H., Kim, K-S., Kim, H., Linton J., Lee, J-G., Effects of TNF-x and IL-1 B on Mucin, Lysozyme, IL-6 and IL-8 in Passage-2 Normal Human Nasal Epithelial Cells, *ACTA Oto-Laryngologica* (Stockholm, Sweden), 1999, 905-910, 119(8).

Yoshida A., Fujihara, T., Nakata, K., Cyclosporin A Increases Tear Fluid Secretion via Release of Sensory Neurotransmitters and Muscarinic Pathway in Mice, *Experimental Eye Research*, May 1999, 541-546, 68(5).

Koichi Ito, Comb Polymers [Poly(ethylene oxide) Side Chains] in Concise Polymeric Materials Encyclopedia 1999, 269-271.

* cited by examiner

OPHTHALMIC COMPOSITIONS COMPRISING POLYETHER SUBSTITUTED POLYMERS

FIELD OF THE INVENTION

The present invention relates to ophthalmic compositions comprising polyether substituted polymers. More specifically, the present invention relates to ophthalmic formulations, solutions and devices comprising polyether substituted polymers.

Dry eye syndrome is an ocular surface disorder, which leads to severe irritation, redness, and itchiness of the eye. The problem may arise from disruptions in any one of the three major components of the tear film, namely the lipid, aqueous, and mucous layers, or from abnormalities in the expression of their constituent molecules.

of dry eye treatments involve the use of inorganic salts, viscous solutions of hydrophilic polymers, and combinations of the two as topical applications. It has been reported that an exponential loss of tear fluid occurs via the puncta upon instillation of artificial tear substitutes. Accordingly, is not limited to soft contact lenses, hard contact lenses, intraocular lenses, overlay lenses, ocular inserts, and optical inserts.

The compositions of the present invention comprise, consist essentially and consist of at least one lens forming component and at least one water soluble polymer. As used herein the term water soluble, means both soluble in water at or above room temperature as well as dispersible in water at or above room temperature. Water soluble polymers of the present invention comprise linear or branched polyether pendant groups having a molecular weight of at least about 300. The water soluble polymers have a weight average molecular weight of at least about 300,000 Daltons, preferably greater than about 500,000; more preferably greater than about 800,000 Daltons. The weight average molecular weight may be measured via gel permeation chromatography against appropriate standards, such as polymethyl methacrylate.

Suitable polyether pendant groups may be derived from monomers of the Formula I

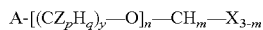

$$A\text{-}[(CZ_pH_q)_y\text{--}O]_n\text{--}CH_m\text{--}X_{3\text{-}m}$$

wherein n is greater than or equal to 7; m is 1 or 2; Z is a $C_1$-$C_6$ substituted or unsubstituted alkyl group, q is 0, 1 or 2 and p is 2-q, y is 2 to 4, A is any free radical polymerizable group and X is a substituent independently selected from the group consisting of H, hydroxyl, unsubstituted straight or branched alkyl groups, substituted straight or branched alkyl groups, substituted and un substituted amines, substituted and unsubstituted amides, mercaptans, ethers and esters.

Examples of free radical polymerizable groups include acrylates, styryls, vinyls, vinyl ethers, $C_{1-6}$alkylacrylates, acrylamides, $C_{1-6}$alkylacrylamides, N-vinyllactams, N-vinylamides, $C_{2-12}$alkenyls, $C_{2-12}$alkenylphenyls, $C_{2-12}$alkenylnaphthyls, or $C_{2-6}$alkenylphenyl$C_{1-6}$alkyls. Preferred free radical polymerizable groups include methacrylates, acryloxys, methacrylamides, acrylamides, and mixtures thereof.

Preferably X is selected from substituted or unsubstituted straight or branched C1-16 alkyl groups, and more preferably from substituted or unsubstituted straight or branched C1-12 alkyl groups.

Substituents on the substituted alky groups for X include carboxylic acids, esters, acyl halides, amines, amides, ketones, aldehydes, halides, sulfides, mercaptans, quartenary ammonium salts combinations thereof and the like.

Substituents on the substituted alky groups for Z include hydroxyl, carboxylic acids, esters, acyl halides, amines, amides, ketones, aldehydes, halides, sulfides, mercaptans, quartenary ammonium salts combinations thereof and the like Preferably n is 7 to 50 and more preferably 7 to 40.

Examples of monomers of Formula I include polymerizable ethoxylated methanols having seven or more ether linkages, such as but not limited to mPEG 350, mPEG 475, mPEG1100, greater homologues thereof, combinations thereof and the like. Preferred monomers of Formula I include mPEG 350, mPEG 475, mPEG 1100 combinations thereof and the like. Suitable monomers may be purchased from various sources such as Aldrich, under the name polyethylene glycol methylether methacrylate, with an average molecular weight within the ranges stated herein.

The water soluble polymer may further comprise pendant groups derived from comonomers. Suitable comonomers may be hydrophilic or hydrophobic and include polymerizable silicones, sugars, carbohydrates, polyethers, amides, lactams, sulfonic acids, sulfonates, amines, hydroxyls, ethers, esters, aldehydes, ketones, amino acids, methacrylated long chain hydrocarbons, polymerizable ionic compounds, reactive latent compounds which may be converted to ionic groups after the water soluble polymer is polymerized, combinations thereof and the like. Preferably suitable comonomers include polymerizable amides, lactams, polymerizable ionic compounds and glycosylated materials. Specific examples of copolymers include lauryl methacrylate, butyl methacrylate, isopropyl methacrylate, methyl methacrylate, phenyl methacrylate, hydroxyethyl methacrylate, methacrylic acid, glycerol monomethacrylate, hydroxyethyl methacrylamide, 2-(-4-morpholinyl)ethyl methacrylate, morpholinyl methacrylamide, 2-(N,N-dimethylamino)ethyl methacrylate, dimethylacrylamide, N-vinyl polymerizable materials including N-vinyl-N-methylacetamide and N-vinyl pyrrolidone, styrene sulfonate, sodium 2-acrylamido-2-methyl-1-propanesulfonate, sulfopropylacrylamide, combinations thereof and the like. Preferred comonomers include dimethylacrylamide, N-vinyl pyrrolidone, combinations thereof and the like.

It is believed that the water soluble polymers of the present invention act as artificial mucins, which help to retain the eyes natural tear film and lipid layer integrity. The many polyether pendant groups provide a hydrophilic, brush or comb-like structure to the water soluble polymers. Thus, in one embodiment, at least about 20%, and preferably at least about 30 of backbone units of the water soluble polymer have a pendant group bound thereto. In yet another embodiment at least about 20%, preferably at least about 60% and more preferably at least about 75% of the pendant groups are polyether pendant groups of Formula I.

The water soluble polymers may be made by a variety of methods including photopolymerization. The selected monomers of Formula I and comonomers are mixed with a photoinitiator, with or without a solvent and polymerized using radiation of the appropriate wavelength.

Suitable photoinitiator systems include aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ether and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998, which is incorporated herein by reference. The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat, visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis (2,6-dimethoxybenzoyl)-2,4-4-trimethylpentyl phosphine oxide (DMBAPO), CGI 1850 and the preferred method of polymerization initiation is visible light.

Suitable solvents include medium to high polarity systems such as toluene, ethyl acetate, tertiary butyl alcohol, methyl sulfoxide, dimethylformamide, methanol, combinations thereof and the like. Preferable solvents are those which are readily miscible with hexanes while preparing a polar polymer, and water soluble solvents while preparing a water immiscible polymer.

The solvent is used in amounts between about 10 and about 90 weight %, based upon the amounts of all components in the reaction mixture (monomer, comonomer, photoinitiator, solvent, etc.).

The reaction mixture is degassed prior to the reaction to remove dissolved oxygen and the reaction is conducted under an inert atmosphere. Polymerization is completed quickly, generally in times less than about 4 hours and preferably less than about 2 hours.

The polymers may be isolated by known techniques, such as precipitation in a non-polar solvent, followed by washing and or reprecipitation processes, and evaporation of the residual solvent. These methods are well known in the art.

The water soluble polymers may be incorporated into a variety of ophthalmic solutions and devices. For example, the water soluble polymers of the present invention may be incorporated into eye drops, contact lens rewetting solutions, contact lens packing and/or cleaning solutions or contact lenses themselves. When the water soluble polymers are included in solutions, suitable amounts include between about 50 ppm by weight and about 5 wt %, and preferably between about 100 ppm and about 3 wt %. When the water soluble polymers are included in contact lenses they may be included in amounts up to about 15 weight % and preferably in amounts between about 0.05 and about 10 weight %. The ophthalmic solutions may include known additional components such as tonicity adjusting agents (such as but not limited to buffers), viscosity adjusting agents, antimicrobial agents, polyelectrolytes, stabilizers, chelants, antioxidants, combinations thereof and the like.

The water soluble polymer may be incorporated into a contact lens in a number of ways, including adding the water soluble polymer to the lens reaction mixture and curing the mixture to form a lens, or soaking a preformed lens in a solution comprising the water soluble polymer, coated onto a lens by any method, including but not limited to grafting, mold transfer, dip coating, spin coating, etc, combinations thereof and the like.

The water soluble-polymer may be incorporated into any contact lens formulation or used with any contact lens. A variety of formulations are known in the art and include etafilcon A, galyfilcon A, lotrafilcon A and B, vifilcon, balafilcon, omafilcon, genfilcon A, lenefilcon A, polymacon, acquafilcon A, and the like. Other lens formulations using polymerizable components known in the art may also be used.

The contact lenses may be hard or soft contact lenses. In one embodiment the contact lenses are soft contact lenses. Soft contact lenses may be made from conventional hydrophilic formulations or silicone hydrogel formulations.

In one embodiment, the water soluble polymers of the present invention are incorporated into the hydrogel formulations without significant covalent bonding to the hydrogel. The absence of significant covalent bonding means that while a minor degree of covalent bonding may be present, it is incidental to the retention of the wetting agent in the hydrogel matrix. Whatever incidental covalent bonding may be present, it would not by itself be sufficient to retain the water soluble polymer in the hydrogel matrix. Instead, the vastly predominating effect keeping the wetting agent associated with the hydrogel is entrapment. The polymer is "entrapped", according to this specification, when it is physically retained within a hydrogel matrix. This is done via entanglement of the polymer chain of the water solublepolymer within the hydrogel polymer matrix. However, van der Waals forces, dipole-dipole interactions, electrostatic attraction and hydrogen bonding can also contribute to this entrapment to a lesser extent.

The water soluble polymers may be incorporated into the hydrogel by a variety of methods. For example, the water'soluble polymers may be added to the reaction mixture such that the hydrogel polymerizes "around" the water soluble polymer, forming a semi-interpenetrating network. Alternatively, the water soluble polymer may be included in the solution in which the lens is packaged. The water soluble polymer permeates into the lens. The packaged lens may be heat treated to increase the amount of water soluble polymer which permeates the lens. Suitable heat treatments, include, but are not limited to conventional heat sterilization cycles, which include temperatures of about 120° C. for times of about 20 minutes. If heat sterilization is not used, the packaged lens may be separately heat treated.

Alternatively, the water soluble polymers may be included in a coating formulation and coated onto at least a portion of an ophthalmic device, and in one embodiment a contact lens via suitable coating method, such as dip coating, mold transfer, spin coating, grafting.

The non-limiting examples below further describe this invention.

The dynamic contact angle or DCA, was measured at 23° C., with borate buffered saline, using a Wilhelmy balance. The wetting force between the lens surface and borate buffered saline is measured using a Wilhelmy microbalance while the sample strip cut from the center portion of the lens is being immersed into the saline at a rate of 100 microns/sec. The following equation is used $$F=2\gamma p \cos \theta \text{ or } \theta=\cos^{-1}(F/2\gamma p)$$

where F is the wetting force, $\gamma$ is the surface tension of the probe liquid, p is the perimeter of the sample at the meniscus and $\theta$ is the contact angle. Typically, two contact angles are obtained from a dynamic wetting experiment—advancing contact angle and receding contact angle. Advancing contact angle is obtained from the portion of the wetting experiment where the sample is being immersed into the probe liquid, and these are the values reported herein. At least four lenses of each composition are measured and the average is reported.

The water content was measured as follows: lenses to be tested were allowed to sit in packing solution for 24 hours. Each of three test lens were removed from packing solution using a sponge tipped swab and placed on blotting wipes which have been dampened with packing solution. Both sides of the lens were contacted with the wipe. Using tweezers, the test lens were placed in a weighing pan and weighed. The two more sets of samples were prepared and weighed as above. The pan was weighed three times and the average is the wet weight.

The dry weight was measured by placing the sample pans in a vacuum oven which has been preheated to 60° C. for 30 minutes. Vacuum was applied until at least 0.4 inches Hg is attained. The vacuum valve and pump were turned off and the lenses were dried for four hours. The purge valve was opened and the oven was allowed reach atmospheric pressure. The pans were removed and weighed. The water content was calculated as follows:

Wet weight =
    combined wet weight of pan and lenses − weight of weighing pan

Dry weight = combined dry weight of pan and lens −
    weight of weighing pan $$\% \text{ water content} = \frac{(\text{wet weight} - \text{dry weight})}{\text{wet weight}} \times 100$$

The average and standard deviation of the water content are calculated for the samples are reported.

Modulus and elongation were measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width was loaded into the grips and elongated at a constant rate of strain of 2 in/min. until it broke. The initial gauge length of the sample (Lo) and sample length at break (Lf) were measured. Twelve specimens of each composition were measured and the average is reported. Tensile modulus was measured at the initial linear portion of the stress/strain curve.

The following abbreviations are used in the examples below:
HEMA 2-hydroxyethyl methacrylate
MAA methacrylic acid
EGDMA ethylene glycol dimethacrylate
mPEG350 polyethylene glycol methylether methacrylate, with a Mn of about 350
mPEG 475 polyethylene glycol methylether methacrylate, with a Mn of about 475
Norbloc 7966 2-(2'-hydroxy-5-methacrylyloxyethylphenyl)-2H-benzotriazole
CGI 1850 1:1 (wgt) blend of 1-hydroxycyclohexyl phenyl ketone and bis(2,6-dimethoxybenzoyl)-2,4-4-trimethyl-pentyl phosphine oxide
CGI-819 bis(2,4,6-trimethylbenzoyl)-phenylphosphineoxide
Blue HEMA the reaction product of Reactive Blue 4 and HEMA, as described in Example 4 of U.S. Pat. No. 5,944,853

EXAMPLES

Example 1

The following compounds in the following amounts were mixed to form a homogenous mixture.

| | |
|---|---|
| mPEG350 | 59.66 g |
| Norbloc 7966 | 340 mg |
| CGI 1850 | 400 mg |
| Isopropyl acetate | 100 mL |

The homogeneous mixture was degassed under a vacuum of 80 mm Hg over a period of one hour. The vacuum was interrupted with a positive nitrogen flow on three to four occasions during the degassing process. The material was moved to a glove box, which was under a nitrogen environment. The mixture was transferred to a crystallizing dish and covered with a watch glass. The system was then exposed to visible light (Philips type Tl03 bulbs) for one hour at room temperature to form the desired polymer.

The polymer was precipitated by the addition of 50 mL of hexanes followed by vigorous agitation. The solvent and any soluble material was decanted. Further washes were performed using 300 mL of hexanes followed by thorough mixing and decantation of the liquids. The washing process was continued until the polymer appeared tacky and very thick.

The product was dissolved in 50 mL of ethyl acetate and reprecipitated by the addition of hexanes to the system. The wash process described above was repeated and the product was rid of all solvent in a rotary evaporator at 55° C. Yield of the desired product was 39 g. The material was obtained as a clear, thick paste whose average molecular weight was determined to be 25000 by GPC.

Example 2

The following compounds in the following amounts were mixed to form a homogenous mixture.

| | |
|---|---|
| mPEG 475 | 45 g |
| tert.butyl alcohol | 70 mL |
| Norbloc | 75 mg |
| CGI1850 | 300 mg |

The homogeneous mixture was degassed for 1 hour under a pressure of 100 mm Hg. The system was purged with nitrogen every 15 minutes during the degassing process. The reaction mixture was transferred to a glove box under a nitrogen atmosphere and into 110 ID×175 OD×70 mm height silvered crystallizing dish. The dish was placed on a shelf approximately 115 mm from the light source (visible light bulbs, Philips—TL03). The vessel was covered with a 2 mm thick filter cover (Schott, VG-6, 339732) and the reactants were polymerized for one hour at room temperature.

The polymer was precipitated in a beaker flask (Buchi—450 mL) with 100 mL of hexanes and vigorous agitation. The liquids were decanted and the polymer was washed twice with 100 mL of hexanes each time. The residual solid was then dissolved in 50 mL of ethyl acetate, reprecipitated and washed with hexanes as described above. The ethyl acetate/hexanes sequence was repeated once more and some of the crude product (2-4 g) removed, dried under reduced pressure, and in a vacuum oven at 50° C. prior to obtaining molecular weight data by GPC.

An accurately weighed amount (W1) of 2-hydroxyethyl methacrylate (HEMA) was added to the beaker flask (approximately 250 g) and the system is gently mixed on a rotary evaporator until the system is completely homogeneous. The bath was then heated at 40° C. under a vacuum of 10-15 mbar. The evaporation was continued for two hours after the point at which no solvent was being distilled over.

The weight of the beaker flask and solution was accurately measured (W2=weight of flask+polymer+HEMA). After transferring the solution to an appropriate container, the beaker flask was thoroughly cleaned, dried, and accurately weighed (W3=weight of beaker flask).

$$W2-W3 = \text{weight of HEMA+polymer} = W4$$

$$W4-W1 = \text{total yield of polymer} = W5 \text{ (typical yield} \approx 45\%)$$

Concentration of the polymer solution (weight percent) was determined as W5/(W4). Molecular weights (Mn) were determined against polymethyl methacrylate (PMMA) standards to be greater than about 300,000.

Example 3

One weight % of the polymer of Example 1 was added to Packing Solution. 5 ml of the Packing Solution polymer mixture was places in glass vials, and a 1-Day ACUVUE brand contact lens (commercially available from Johnson & Johnson) was placed in the vial. The vial was sealed and autoclaved at 121° C. for 30 minutes. The lenses were allowed to equilibrate after autoclaving for at least about 1 day at ambient temperature.

Five subjects were recruited to wear the test lens in one eye and the control lens in their other eye. The lenses were allowed to settle for 30-minutes prior to any observations.

After 30 minutes, the non-invasive tear break-up time (NIBUT) and lipid layer thickness were observed for both lenses using the Tearscope Plus™ (Keeler). The test lens was found to have a longer NIBUT than the control lens (10.4 seconds vs. 7.6 seconds). The test lens was also found to have a thicker lipid layer than the control lens in 4 of the 5 of the subjects.

TABLE 2

| Lipid Pattern | Ex. #3 | 1 · DAY ACUVUE ® |
|---|---|---|
| None | 0% | 0% |
| Open | 0% | 60% |
| Closed | 20% | 20% |
| Flow/Wave | 60% | 0% |
| Amorphous | 20% | 0% |
| Colours | 0% | 20% |

Example 4

The copolymer (MM-44) formed in Example 2 was used as a monomer component in the formulation listed in Table 3, below.

TABLE 3

| Components | Weight % |
|---|---|
| HEMA | 95.88 |
| MAA | 1.50 |
| Norbloc | 1.00 |
| CGI 819 | 0.50 |
| EGDMA | 1.00 |
| BLUE HEMA | 0.02 |
| Ex. _(MM-44) | 0.10 |

The components were mixed in a glass jar with 40 weight % boric acid glyceryl ester, sealed and rolled on ajar roller until homogeneous.

The lenses were were made on a single cavity lens machine utilizing polystyrene +1% zinc front curve and back curve lens molds. Monomer was dosed into the front curve, back curve was deposited, and parts were placed under pre-cure lights for 10 seconds. Molds were cured for 4 minutes at approximately 4 mW/cm² and 65° C. Lenses were demolded and placed into leach solution at 70±5° C. for 180±30 minutes, followed by rinse at 45±5° C. for 15 to 60 minutes and equilibration at 45±5° C. for a minimum of 3 hours. Lenses were visually inspected, packaged in vials with packing solution and sterilized for 30 minutes at 121° C. Physical properties were measured for the lenses and are shown in Table 4, below.

TABLE 4

| Property | |
|---|---|
| Water Content (%) | 53.6 ± 0.1 |
| Modulus (psi) | 50.9 ± 2.6 |
| Elongation (%) | 155.7 ± 49.1 |
| Advancing Contact Angle (°) | 68 ± 6 |

Thirty myopic, current soft contact lens wearers were recruited to wear test lenses and control lenses (1-DAY ACUVUE). Each lens type was worn daily wear for 1-week and replaced on a daily disposable basis. The study design was a randomized, bilateral cross-over design with investigator masking. Twenty-nine subjects completed the study.

After wearing the lenses for 1-week, the subjects completed preference questionnaires comparing their experiences with both lens types. The lenses from this Example 4 were preferred 2:1 over 1-DAY ACUVUE® in the areas of overall comfort, end of day comfort, dryness, wearing time, and moisture. Symptoms reported by the subjects at the 1-week visit were reduced for the test lenses by 50% compared to the control lens.

We claim:

1. A ophthalmic device comprising a polymer matrix and entrapped therein at least one water soluble polymer having a molecular weight of about 500,000 Daltons or greater and comprising linear or branched polyether pendant groups having a molecular weight of about 300 or greater and wherein said polyether pendant groups result from polymerizing monomers of the Formula I

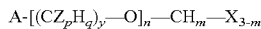

wherein n is 7 or greater; Z is a $C_1$-$C_6$ alkyl group which may be unsubstituted or substituted with hydroxyl, carboxylic acids, esters, acyl halides, amines, amides, ketones, aldehydes, halides, sulfides, mercaptans, quartenary ammonium salts and combinations thereof, q is 0, 1 or 2 and p is 2-q, y is 2 to 4, m is 1 or 2; A is any free radical polymerizable group and X is selected from straight or branched C1-16 alkyl groups which may be unsubstituted or substituted with a substituent independently selected from the group consisting of carboxylic acids, esters, acyl halides, amines, amides, ketones, aldehydes, halides, sulfides, mercaptans, quartenary ammonium salts and combinations thereof.

2. The device of claim 1 wherein X is selected from is selected from substituted or unsubstituted straight or branched C1-12 alkyl groups.

3. The device of claim 1 wherein said alkyl group is substituted with a group selected from the group consisting of carboxylic acids, esters, acyl halides, amines, amides, ketones, aldehydes, halides, sulfides, mercaptans, quartenary ammonium salts and combinations thereof.

4. The device of claim 1 wherein n is an integer of between 7 to 50.

5. The device of claim 1 wherein n is an integer of between 7 to 40.

6. The device of claim 1 wherein said polymer comprises at least 20% backbone units, based upon all backbone units in said polymer, having a pendant group bound thereto.

7. The device of claim 1 wherein said polymer comprises at least 30% backbone units, based upon all backbone units in said polymer, having a pendant group bound thereto.

8. The device of claim 1 wherein at least 20% of said pendant groups, based upon all pendant groups in said polymer, are polyether pendant groups of Formula I.

9. The device of claim 1 wherein at least 60% of said pendant groups, based upon all pendant groups in said polymer, are polyether pendant groups of Formula I.

10. The device of claim 1 wherein at least 75% of said pendant groups, based upon all pendant groups in said polymer, are polyether pendant groups of Formula I.

11. The device of claim 1 wherein said pendant groups further comprise at least one second pendant group selected from the group consisting of silicones, sugars, carbohydrates, polyethers, amides, lactams, sulfonic acids, sulfonates, amines, hydroxyls, ethers, esters, aldehydes, ketones, amino acids, methacrylated long chain hydrocarbons, polymerizable ionic compounds, reactive latent compounds which may be converted to ionic groups after the water soluble polymer is polymerized and combinations thereof.

12. The device of claim 1 wherein said pendant groups further comprise at least one second pendant group selected from the group consisting of amides, lactams, glycosylated materials, polymerizable ionic compounds and combinations thereof.

13. The device of claim 1 wherein said pendant groups further comprise at least one second pendant group selected from the group consisting lauryl methacrylate, butyl methacrylate, isopropyl methacrylate, methyl methacrylate, phenyl methacrylate, hydroxyethyl methacrylate, methacrylic acid, glycerol monomethacrylate, hydroxyethyl methacrylamide, 2-(-4-morpholinyl)ethyl methacrylate, morpholinyl methacrylamide, 2-(N,N-dimethylamino)ethyl methacrylate, dimethylacrylamide, N-vinyl pyrrolidone, N-vinyl-N-methylacetamide, styrene sulfonate, sodium 2-acrylamido-2-methyl-1-propanesulfonate, sulfopropylacrylamide and combinations thereof.

14. The ophthalmic device of claim 1 wherein said water soluble polymer is entrapped in said polymer matrix without substantial covalent bonding.

* * * * *